United States Patent
Arts

(10) Patent No.: US 9,554,845 B2
(45) Date of Patent: Jan. 31, 2017

(54) SURGICAL FORCEPS FOR TREATING AND CUTTING TISSUE

(71) Applicant: COVIDIEN LP, Mansfield, MA (US)

(72) Inventor: Gene H. Arts, Berthoud, CO (US)

(73) Assignee: COVIDIEN LP, Mansfield, MA (US)

( * ) Notice: Subject to any disclaimer, the term of this patent is extended or adjusted under 35 U.S.C. 154(b) by 355 days.

(21) Appl. No.: 14/183,090

(22) Filed: Feb. 18, 2014

(65) Prior Publication Data

US 2015/0025528 A1 Jan. 22, 2015

Related U.S. Application Data

(60) Provisional application No. 61/847,857, filed on Jul. 18, 2013.

(51) Int. Cl.
*A61B 18/14* (2006.01)
*A61B 17/29* (2006.01)
*A61B 18/00* (2006.01)

(52) U.S. Cl.
CPC ....... *A61B 18/1445* (2013.01); *A61B 18/1447* (2013.01); *A61B 2017/2926* (2013.01);
(Continued)

(58) Field of Classification Search
CPC ............ A61B 18/1442; A61B 18/1445; A61B 18/1447; A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | | |
|---|---|---|---|
| 2,796,065 A * | 6/1957 | Kapp | A61B 17/282 606/207 |
| D249,549 S | 9/1978 | Pike | |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 13/731,674, filed Dec. 31, 2012; inventor: Siebrecht.
(Continued)

*Primary Examiner* — Jaymi Della

(57) ABSTRACT

An end effector assembly includes a first jaw member defining a wedge configuration having first and second planar surfaces angled inwardly to an apex, and a second jaw member defining a nest configuration having a cut-out defined by third and fourth planar surfaces angled inwardly to a trough. The jaw members are movable between spaced-apart position and approximated positions. In the approximated position, the first and third and second and fourth planar surfaces are disposed in parallel orientation relative to one another imparting a first grasping pressure to tissue disposed therebetween, while the apex is received within the trough imparting a second grasping pressure to tissue disposed therebetween. The jaw members are adapted to connect to a source of energy for conducting energy between the parallel planar surfaces to create a pair of tissue seals, and between the apex and trough to cut tissue between the tissue seals.

17 Claims, 4 Drawing Sheets

(52) U.S. Cl.
CPC ............... *A61B 2018/0063* (2013.01); *A61B 2018/00601* (2013.01); *A61B 2018/00922* (2013.01); *A61B 2018/00958* (2013.01); *A61B 2018/1452* (2013.01)

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,626,578 A * | 5/1997 | Tihon ............... A61B 18/1442 606/48 |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,083,223 A * | 7/2000 | Baker ............... A61B 18/1445 606/49 |
| 6,113,598 A * | 9/2000 | Baker ............... A61B 18/1445 606/38 |
| H1904 H | 10/2000 | Yates et al. |
| 6,267,761 B1 | 7/2001 | Ryan |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,679,882 B1 | 1/2004 | Kornerup |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,931,649 B2 | 4/2011 | Couture et al. |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,597,297 B2 | 12/2013 | Couture et al. |
| 8,647,343 B2 | 2/2014 | Chojin et al. |
| 8,679,115 B2 | 3/2014 | Reschke |
| 2003/0229344 A1 * | 12/2003 | Dycus ............... A61B 18/1445 606/51 |
| 2004/0078035 A1 * | 4/2004 | Kanehira ........... A61B 17/3201 606/28 |
| 2005/0101965 A1 * | 5/2005 | Ryan ................. A61B 18/1442 606/96 |
| 2006/0271038 A1 * | 11/2006 | Johnson ........... A61B 17/07207 606/45 |
| 2007/0185487 A1 * | 8/2007 | Hafner .............. A61B 18/1442 606/45 |
| 2008/0015567 A1 * | 1/2008 | Kimura ............. A61B 18/1442 606/41 |
| 2008/0058802 A1 | 3/2008 | Couture et al. |
| 2008/0195093 A1 | 8/2008 | Couture et al. |
| 2011/0071523 A1 | 3/2011 | Dickhans |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |

(56) References Cited

FOREIGN PATENT DOCUMENTS

| | | | |
|---|---|---|---|
| JP | 2000-102545 A | 4/2000 | |
| JP | 2000-135222 A | 5/2000 | |
| JP | 2000342599 A | 12/2000 | |
| JP | 2000350732 A | 12/2000 | |
| JP | 2001008944 A | 1/2001 | |
| JP | 2001-29355 | 2/2001 | |
| JP | 2001029356 A | 2/2001 | |
| JP | 2001-03400 | 4/2001 | |
| JP | 2001128990 A | 5/2001 | |
| JP | 2001-190564 A | 7/2001 | |
| JP | 2002-136525 A | 5/2002 | |
| JP | 2002-528166 A | 9/2002 | |
| JP | 2003-116871 A | 4/2003 | |
| JP | 2003-175052 A | 6/2003 | |
| JP | 2003245285 A | 9/2003 | |
| JP | 2004-517668 A | 6/2004 | |
| JP | 2004-528869 A | 9/2004 | |
| JP | 2005-152663 A | 6/2005 | |
| JP | 2005-253789 A | 9/2005 | |
| JP | 2005312807 A | 11/2005 | |
| JP | 2006-015078 A | 1/2006 | |
| JP | 2006-501939 A | 1/2006 | |
| JP | 2006-095316 A | 4/2006 | |
| JP | 2008-054926 A | 3/2008 | |
| JP | 2011125195 A | 6/2011 | |
| SU | 401367 A1 | 11/1974 | |
| WO | 0036986 A1 | 6/2000 | |
| WO | 0059392 A1 | 10/2000 | |
| WO | 0115614 A1 | 3/2001 | |
| WO | 0154604 A1 | 8/2001 | |
| WO | 0245589 A3 | 9/2002 | |
| WO | 2006/021269 A1 | 3/2006 | |
| WO | 2005110264 A3 | 4/2006 | |
| WO | 2008/040483 A1 | 4/2008 | |
| WO | 2011/018154 A1 | 2/2011 | |

OTHER PUBLICATIONS

U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.

* cited by examiner

SURGICAL FORCEPS FOR TREATING AND CUTTING TISSUE

CROSS REFERENCE TO RELATED APPLICATION

The present application claims the benefit of and priority to U.S. Provisional Application Ser. No. 61/847,857, filed on Jul. 18, 2013, the entire contents of which are incorporated herein by reference.

BACKGROUND

Technical Field

The present disclosure relates to surgical devices and, more particularly, to surgical forceps and end effector assemblies thereof for treating, e.g., sealing, and/or cutting tissue.

Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to coagulate and/or cauterize tissue. Certain surgical procedures require more than simply cauterizing tissue and rely on the unique combination of grasping pressure, precise energy control and gap distance (i.e., distance between opposing jaw members when closed about tissue) to "seal" tissue. Typically, once tissue is sealed, the surgeon has to accurately sever the tissue along the newly formed tissue seal. Accordingly, many tissue sealing devices have been designed which incorporate a knife or blade member which effectively severs the tissue after forming a tissue seal. More recently, tissue sealing devices have incorporated energy-based cutting features for energy-based tissue division.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, an end effector assembly of a surgical forceps is provided. The end effector assembly includes first and second jaw members. The first jaw member defines a wedge configuration having first and second planar surfaces angled inwardly to an apex. The second jaw member is complementary to the first jaw member and defines a nest configuration having a cut-out defined by third and fourth planar surfaces angled inwardly to a trough. One or both of the jaw members is movable relative to the other between a spaced-apart position and an approximated position for grasping tissue therebetween. In the approximated position, the first and third planar surfaces are disposed in parallel orientation relative to one another imparting a first grasping pressure to tissue disposed therebetween, the second and fourth planar surfaces are disposed in parallel orientation relative to one another imparting the first grasping pressure to tissue disposed therebetween, and the apex is received within the trough imparting a second, greater grasping pressure to tissue disposed therebetween. One or both of the jaw members is adapted to connect to a source of energy for conducting energy between: the first and third planar surfaces and through tissue grasped therebetween to create a first tissue seal, the second and fourth planar surfaces and through tissue grasped therebetween to create a second tissue seal, and between the apex and trough and through tissue grasped therebetween to cut tissue between the first and second tissue seals.

In an aspect of the present disclosure, each jaw member includes an electrically-conductive tissue-contacting plate disposed on an opposed surface thereof. More specifically, the electrically-conductive tissue-contacting plate of the first jaw member may define a first planar portion disposed about the first planar surface, a second planar portion disposed about the second planar surface, and a cap portion disposed about the apex and interconnecting the first and second planar portions. The electrically-conductive tissue-contacting plate of the second jaw member may define a third planar portion disposed about the third planar surface, a fourth planar portion disposed about the fourth planar surface, and an inverted cap portion disposed about the trough and interconnecting the third and fourth planar portions. Further, the electrically-conductive tissue-contacting plates of each jaw member may be monolithically formed as a single component, although other configurations are also contemplated.

In another aspect of the present disclosure, each of the jaw members includes a proximal flange portion and a distal jaw portion. The distal jaw portion of each jaw member includes a jaw housing, an insulative body supported on the jaw housing, and the electrically-conductive tissue-contacting plate disposed about and conformed to the insulative body.

In yet another aspect of the present disclosure, the proximal flange portions of the jaw members are pivotable coupled to one another for pivoting the jaw members relative to one another between the spaced-apart and approximated positions.

In still another aspect of the present disclosure, the apex and/or trough are configured to establish a region of increased current concentrations adjacent thereto upon conduction of energy therebetween to facilitate tissue cutting and/or a region of increased tension on tissue to facilitate tissue cutting.

A surgical system is also provided in accordance with the present disclosure. The surgical system includes an energy source and a surgical forceps. The surgical forceps includes an end effector assembly having first and second jaw members. The first jaw member defines a wedge configuration having first and second planar surfaces angled inwardly to an apex. The second jaw member is complementary to the first jaw member and defines a nest configuration having a cut-out defined by third and fourth planar surfaces angled inwardly to a trough. One or both of the jaw members is movable relative to the other between a spaced-apart position and an approximated position for grasping tissue therebetween. In the approximated position, the first and third planar surfaces are disposed in parallel orientation relative to one another imparting a first grasping pressure to tissue disposed therebetween, the second and fourth planar surfaces are disposed in parallel orientation relative to one another imparting the first grasping pressure to tissue disposed therebetween, and the apex is received within the trough imparting a second, greater grasping pressure to tissue disposed therebetween. One or both of the jaw members is coupled to the energy source for conducting energy between: the first and third planar surfaces and through tissue grasped therebetween to create a first tissue seal, the second and fourth planar surfaces and through tissue grasped therebetween to create a second tissue seal, and between the apex and trough and through tissue grasped therebetween to cut tissue between the first and second tissue seals.

In an aspect of the present disclosure, the energy source is a generator. Further, the generator may be configured to supply electrosurgical energy to one or both of the jaw members.

In another aspect of the present disclosure, the surgical forceps further includes an activation assembly for selectively supplying energy from the generator to the jaw member(s).

In still another aspect of the present disclosure, the generator is configured to supply a first energy algorithm to the jaw member(s) for sealing tissue and a second energy algorithm to the jaw member(s) for cutting tissue.

In still yet another aspect of the present disclosure, the activation assembly includes a two-mode activation switch configured to selectively supply energy from the generator to the jaw member(s) in a first mode corresponding to the first energy algorithm and a second mode corresponding to the second energy algorithm.

In another aspect of the present disclosure, each of the jaw members includes a proximal flange portion and a distal jaw portion. The distal jaw portion of each jaw member includes a jaw housing, an insulative body supported on the jaw housing, and an electrically-conductive tissue-contacting plate disposed about and conformed to the insulative body.

In yet another aspect of the present disclosure, the electrically-conductive tissue-contacting plate of the first jaw member defines a first planar portion disposed about the first planar surface, a second planar portion disposed about the second planar surface, and a cap portion disposed about the apex and interconnecting the first and second planar portions; and the electrically-conductive tissue-contacting plate of the second jaw member defines a third planar portion disposed about the third planar surface, a fourth planar portion disposed about the fourth planar surface, and an inverted cap portion disposed about the trough and interconnecting the third and fourth planar portions.

In yet another aspect of the present disclosure, the proximal flange portions of the jaw members are pivotable coupled to one another for pivoting the jaw members relative to one another between the spaced-apart and approximated positions.

In still another aspect of the present disclosure, the surgical forceps further includes a shaft having the end effector assembly disposed at a distal end thereof and a handle assembly disposed at a proximal end thereof. The handle assembly is operably coupled to the end effector assembly and is selectively actuatable for moving the jaw members between the spaced-apart and approximated positions.

In yet another aspect of the present disclosure, the surgical forceps further includes first and second shaft members coupled to the first and second jaw members, respectively. The first and second shaft members are movable relative to one another between an open position and a closed position for pivoting the jaw members relative to one another between the spaced-apart and approximated positions.

In still yet another aspect of the present disclosure, the apex and/or trough are configured to establish a region of increased current concentrations adjacent thereto upon conduction of energy therebetween to facilitate tissue cutting and/or a region of increased tension on tissue to facilitate tissue cutting.

A method of treating tissue is also provided in accordance with the present disclosure. The method includes grasping tissue between first and second jaw members such that a first portion of tissue is grasped between a first pair of parallel surfaces of the jaw members under a first grasping pressure, a second portion of tissue is grasped between a second pair of parallel surfaces of the jaw members under the first grasping pressure, and a third portion of tissue disposed between the first and second portions of tissue is grasped between the jaw members under a second, greater grasping pressure. The portions of the jaw members grasping the third portion of tissue are configured to establish increased current concentrations adjacent thereto upon conduction of energy therebetween. The method further includes conducting energy between the jaw members such that the first and second portions of tissue are sealed and such that the increased grasping pressure and current concentrations adjacent the third portion of tissue facilitate electrical cutting of tissue to divide tissue between the tissue seals.

BRIEF DESCRIPTION OF THE DRAWINGS

Various aspects and features of the present disclosure are described herein with reference to the drawings wherein.

DETAILED DESCRIPTION

Figure 1:
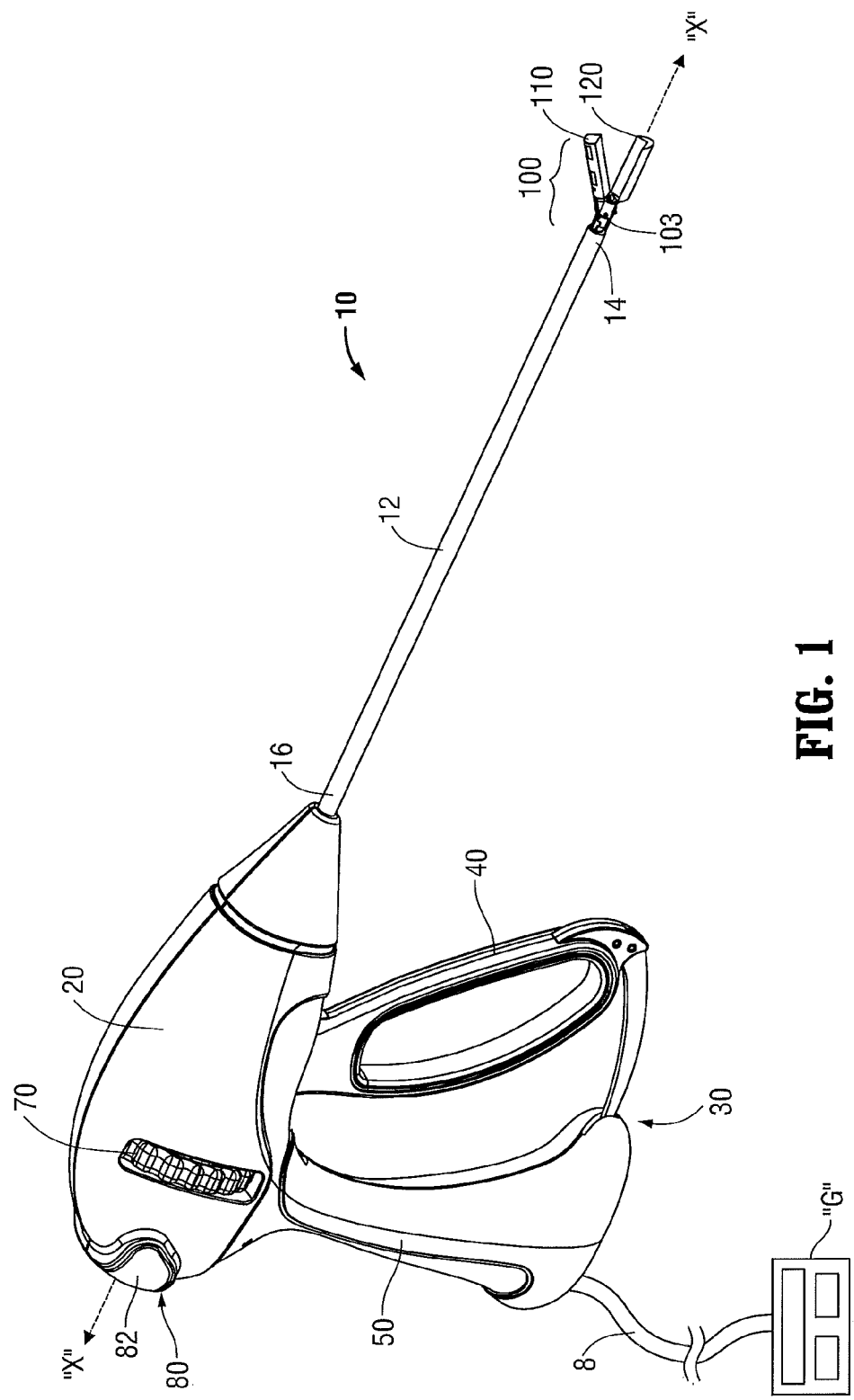
FIG. 1 is a front, side, perspective view of an endoscopic surgical forceps configured for use in accordance with the present disclosure.
Figure 2:
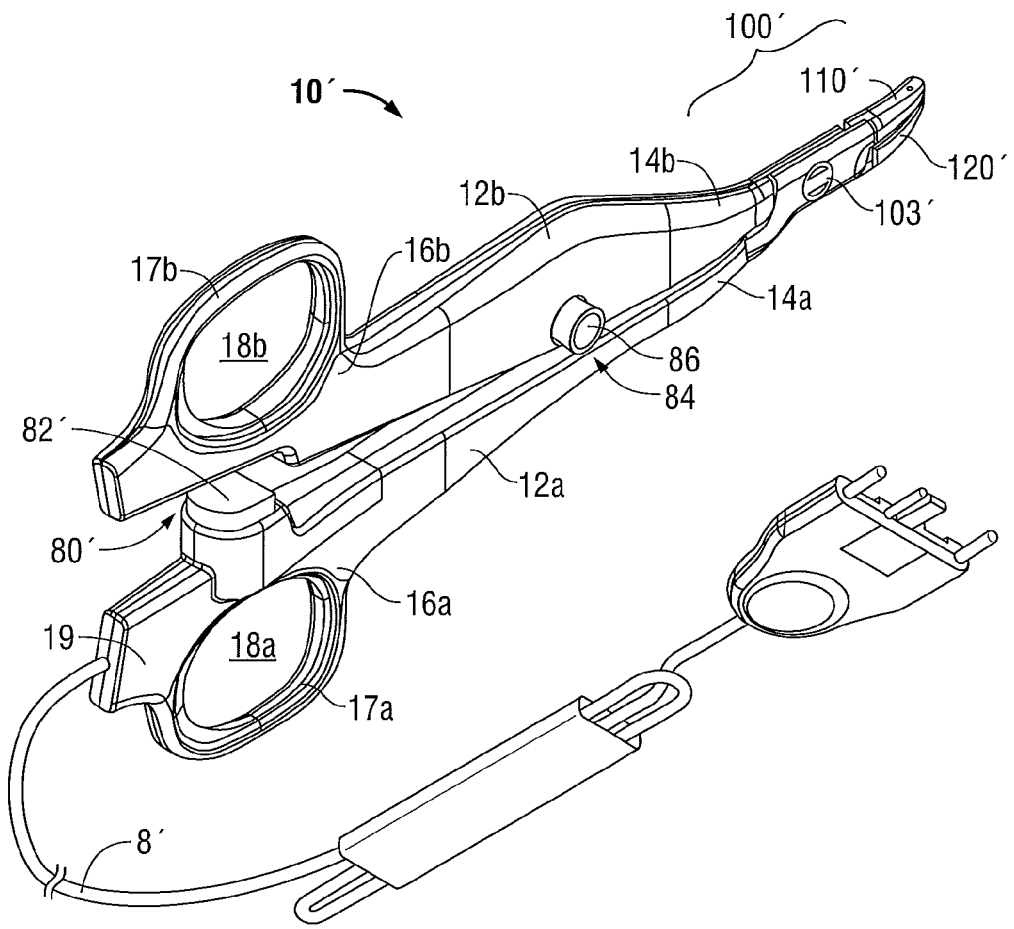
FIG. 2 is a front, side, perspective view of an open surgical forceps configured for use in accordance with the present disclosure.

Turning to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic device, e.g., forceps 10, an open device, e.g., forceps 10', or any other suitable surgical device may be utilized in accordance with the present disclosure. Obviously, different electrical and mechanical connections and considerations apply to each particular type of device; however, the aspects and features of the present disclosure remain generally consistent regardless of the particular device used.

Referring to FIG. 1, an endoscopic forceps 10 is provided defining a longitudinal axis "X" and including a housing 20, a handle assembly 30, a rotating assembly 70, an activation assembly 80, and an end effector assembly 100. Forceps 10 further includes a shaft 12 having a distal end 14 configured to mechanically engage end effector assembly 100 and a proximal end 16 that mechanically engages housing 20. A cable 8 connects forceps 10 to an energy source, e.g., generator "G," although forceps 10 may alternatively be configured as a battery-powered device. Cable 8 includes a wire (or wires) 9 (FIG. 3B) extending therethrough that has sufficient length to extend through shaft 12 in order to provide energy to at least one of tissue-contacting plates 114, 124 (FIGS. 3A-3B) of jaw members 110, 120, respectively. Activation assembly 80 includes an activation switch 82 provided on housing 20 for selectively supplying energy to jaw members 110, 120 for treating, e.g., sealing, tissue and/or cutting tissue. More specifically, activation switch 82 may be configured as a two-mode activation switch 82 for sealing tissue (the first mode), and for energy-based tissue cutting (the second mode). Switching between the two modes may be performed automatically, e.g., after completion of tissue sealing in the first mode the second mode is initiated to cut the sealed tissue, or manually, e.g., a first activation or activation of a first portion of activation switch 82 may initiate the first mode for tissue sealing while a second activation or activation of a second portion of activation switch 82 may initiate the second mode for tissue cutting.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of jaw members 110, 120 between a spaced-apart position and an approximated position to grasp tissue between jaw members 110, 120. More specifically, as shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. Rotating assembly 70 is rotatable in either direction about longitudinal axis "X" to rotate end effector assembly 100 about longitudinal axis "X."

Referring to FIG. 2, an open forceps 10' is shown including two elongated shaft members 12a, 12b, each having a proximal end 16a, 16b, and a distal end 14a, 14b, respectively. Forceps 10' is configured for use with an end effector assembly 100' similar to end effector assembly 100 (FIG. 1). More specifically, end effector assembly 100' includes first and second jaw members 110', 120' attached to respective distal ends 14a, 14b of shaft members 12a, 12b. Jaw members 110', 120' are pivotably connected about a pivot 103'. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of shaft members 12a, 12b relative to one another to, in turn, pivot jaw members 110', 120' from an open position, wherein jaw members 110', 120' are disposed in spaced-apart relation relative to one another, to a closed position, wherein jaw members 110', 120' cooperate to grasp tissue therebetween.

One of the shaft members 12a, 12b of forceps 10', e.g., shaft member 12a, includes a proximal shaft connector 19 configured to connect the forceps 10' to generator "G" (FIG. 1) or other suitable energy source. Proximal shaft connector 19 secures a cable 8' to forceps 10' such that the user may selectively supply energy, e.g., electrosurgical energy, to jaw members 110', 120' for treating, e.g., sealing, tissue and/or for energy-based tissue cutting. More specifically, a first activation assembly 80' is provided for supplying energy to jaw members 110', 120' to treat tissue upon sufficient approximation of shaft members 12a, 12b, e.g., upon activation of activation button 82' via shaft member 12b. A second activation assembly 84 including a selectively depressible activation button 86 is provided on one of the shaft members 12a, 12b, e.g., shaft member 12b, for selectively supplying energy, e.g., electrosurgical energy, to either or both of jaw members 110', 120' for energy-based tissue cutting. Alternatively, a single, two-mode activation assembly may be provided, similarly as described above with respect to forceps 10 (FIG. 1).

Figure 3A:
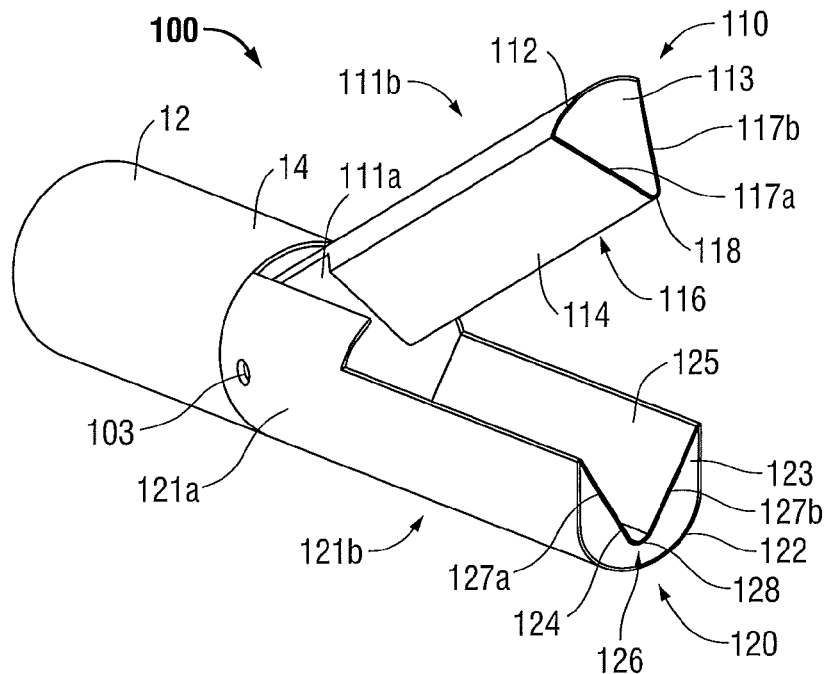
FIG. 3A is a front, side, perspective view of an end effector assembly configured for use with the forceps of FIG. 1 or 2.
Figure 3B:
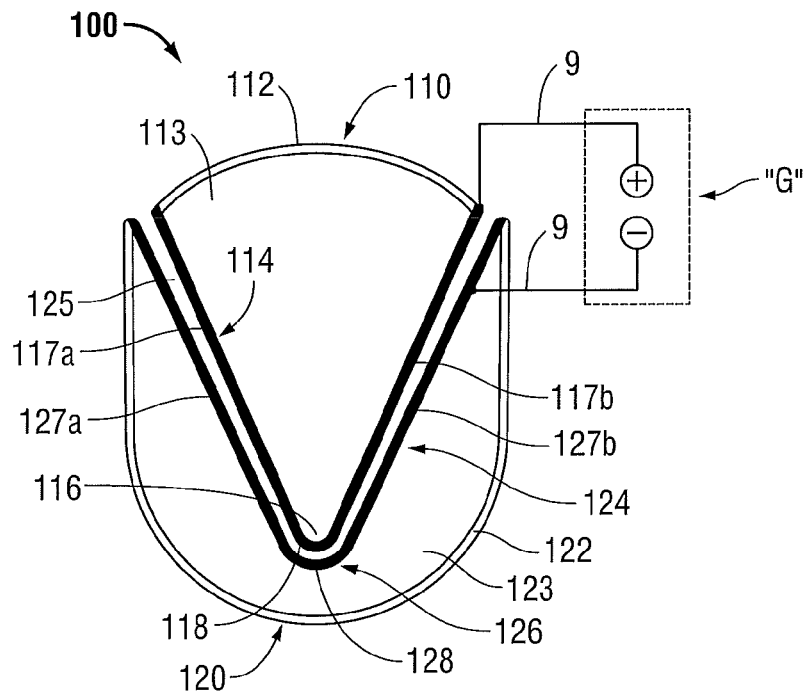
FIG. 3B is a transverse, cross-sectional view of the end effector assembly of FIG. 3A.

With reference to FIGS. 3A and 3B, end effector assembly 100 of forceps 10 (FIG. 1) is shown and described. End effector assembly 100 may similarly be used in conjunction with forceps 10' (FIG. 2), or any other suitable surgical device. For purposes of simplicity, end effector assembly 100 is described herein as configured for use with forceps 10 (FIG. 1). Further, end effector assembly 100' (FIG. 2) is similar to and may incorporate any of the features of end effector assembly 100, described below, but will not be described hereinbelow to avoid unnecessary repetition.

Each jaw member 110, 120 of end effector assembly 100 includes a proximal flange portion 111a, 121a and a distal jaw portion 111b, 121b, respectively. Proximal flange portions 111a, 121a of jaw members 110, 120 are pivotably coupled to one another about pivot 103 and to the drive assembly (not shown), thus permitting pivotable movement of jaw members 110, 120 between the spaced-apart and approximated positions upon actuation of movable handle 40 (FIG. 1). Distal jaw portions 111b, 121b of jaw members 110, 120 extend proximally from respective proximal flange portions 111a, 121a and each include a jaw housing 112, 122 supporting an insulative body 113, 123, and a tissue-contacting plate 114, 124 disposed on the respective insulative body 113, 123 thereof. More specifically, tissue-contacting plates 114, 124 are disposed about and conform to the opposed surfaces of respective insulative bodies 113, 123 such that, upon movement of jaw members 110, 120 to the approximated position, tissue is grasped between tissue-contacting plates 114, 124.

Continuing with reference to FIGS. 3A-3B, Insulative bodies 113, 123 of jaw members 110, 120 are complementary to one another and cooperate to define a nested wedge configuration when disposed in the approximated position, as best shown in FIG. 3B. More specifically, one of the insulative bodies 113, 123, e.g., insulative body 113 of jaw member 110, defines a generally triangular-shaped cross-sectional configuration with an apex 116 oriented towards jaw member 120, while the other insulative body 113, 123, e.g., insulative body 123 of jaw member 120, defines a cut-out 125 having a generally triangular-shaped cross-sectional configuration and defining a trough 126 oriented to oppose jaw member 110. However, this configuration may be reversed, e.g., wherein insulative body 113 of jaw member 110 includes the trough and wherein insulative body 123 of jaw member 120 includes the apex. Cut-out 125 of insulative body 123 is dimensioned similar to or slightly larger than insulative body 113 such that, upon approximation of jaw members 110, 120, insulative body 113 is received within cut-out 125 in a nested wedge configuration. That is, as a result of the above-described configuration, one of the jaw members, e.g., jaw member 110, serves as the wedge, while the other jaw member, e.g., jaw member 120, serves as the nest configured to receive the wedge within the cut-out thereof upon approximation of jaw members 110, 120.

Each tissue-contacting plate 114, 124 is formed from an electrically conductive material and defines a monolithic configuration, although segmented configurations are also contemplated. Although described herein as configured for conducting electrical energy, e.g., electrosurgical energy, therebetween for treating and/or cutting tissue, tissue-contacting plates 114, 124 may alternatively be configured to conduct any suitable energy through tissue grasped therebetween for energy-based tissue treatment and/or cutting. Tissue-contacting plates 114, 124, as mentioned above, are disposed about and conform to the opposed surfaces of respective insulative bodies 113, 123. As such, tissue-contacting plate 114 includes a pair of generally planar angled portions 117a, 117b that are angled inwardly towards apex 116 and are interconnected via a curved cap portion 118 disposed about apex 116. Tissue-contacting plate 124, on the other hand, includes a pair of generally planar angled portions 127a, 127b that are angled inwardly towards trough 126 and are interconnected via an inverted curved cap portion 128 shaped complementary to curved cap portion 118 and disposed about trough 126. In the approximated position of jaw members 110, 120, as best shown in FIG. 3B, planar angled portions 117a, 127a and planar angled portions 117b, 127b are positioned to oppose one another in substantially parallel orientation relative to one another, while cap portion 118 is received within inverted cap portion 128. The importance of this configuration will be detailed below.

Referring additionally to FIG. 1, tissue-contacting plates 114, 124 are coupled to activation switch 82 and generator "G," or other suitable source of energy, e.g., via wires 9 extending from cable 8 through forceps 10, such that energy, e.g., electrosurgical energy, may be selectively supplied to tissue-contacting plate 114 and/or tissue-contacting plate 124 to establish a potential gradient therebetween and conduct energy between tissue-contacting plates 114, 124 and through tissue grasped between jaw members 110, 120 to treat, e.g., seal, and/or cut tissue, e.g., upon activation of activation switch 82. As a result of the above-described configuration of tissue-contacting plates 114, 124 and jaw members 110, 120, energy is conducted between the generally parallel planar angled portions 117a, 127a and the generally parallel planar angled portions 117b, 127b and through tissue grasped therebetween to seal tissue on either side of the apex and trough 116, 126, and is conducted between cap portion 118 and inverted cap portion 128 and through tissue grasped between the apex and trough 116, 126, respectively, to electrically cut tissue between the two tissue seals.

As mentioned above, activation switch 82 may be configured as a two-mode activation switch 82 for sealing tissue (the first mode), and for energy-based tissue cutting (the second mode), and may be switched between the two modes manually or automatically. This two-mode configuration allows for different energy-delivery algorithms incorporated into generator "G" to be utilized for the sealing mode and the cutting mode. Alternatively, activation switch 82 may be configured as a single-mode switch such that, upon activation, energy is supplied to jaw members 110, 120 for both sealing and cutting tissue grasped between jaw members 110, 120. In either configuration, the nested wedge configuration of jaw members 110, 120 detailed above facilitates both the sealing and cutting of tissue, as will be described in greater detail below.

The above-described nested wedge configuration of jaw members 110, 120 of end effector assembly 100 provides numerous advantages, both mechanical and electrical. In particular, the nested wedge configuration of jaw members 110, 120 provides a mechanical advantage (MA) of the wedge, e.g., jaw member 110, according to the following expression:

$$MA=\frac{1}{2}(1/\sin(\theta/2)),$$

where $\theta$ is the angle between the planar angled portions 117a, 117b. Thus, a 30° wedge, for example, would impart an approximately 1.93 greater grasping pressure on tissue grasped between the jaw members 110, 120 as compared to the clamping force imparted to jaw members 110, 120, e.g., a mechanical advantage of 1.93. The mechanical advantage (MA) may also be expressed according to the following expression:

$$MA=H/W,$$

where H is the height of jaw member 110 (as viewed in FIG. 3B) and W is the maximum width of jaw member 110 (as viewed in FIG. 3B). Thus, with the height H of jaw member being equal to twice the width W, for example, a mechanical advantage of 2 can be achieved.

The nested wedge configuration of jaw members 110, 120 of end effector assembly 100 further provides for greater seal widths, e.g., the widths extending along angled portions 117a, 127a and 117b, 127b between which tissue is sealed, without necessitating an increase in the overall width dimension of jaw members 110, 120. The nested wedge configuration also allows for self-alignment of the jaw members 110, 120. Further, as a result of the complementary configurations of insulative bodies 113, 123, the planar angled portions 117a, 127a and 117b, 127b of tissue-contacting plates 114, 124 are substantially parallel to one another when grasping tissue therebetween, thus ensuring a uniform gap distance between the planar angled portions 117a, 127a and 117b, 127b of tissue-contacting plates 114, 124 and a consistent grasping pressure applied to tissue disposed therebetween. Each of the above-noted features contributes to formation of an effective tissue seal.

The nested wedge configuration of jaw members 110, 120 also facilitates effective and efficient electrical cutting of tissue grasped between the tissue seals created between angled portions 117a, 127a and 117b, 127b, e.g., between cap portion 118 and inverted cap portion 128. In particular, the geometry of the nested wedge configuration of jaw members 110, 120 creates an area of increased grasping pressure between and adjacent cap portion 118 and inverted cap portion 128. Such a feature is advantageous in that, it has been found that increased pressure facilitates effective electrical tissue cutting as compared to the pressure required for tissue sealing. Accordingly, the above-described configuration obviates the need to apply a first grasping pressure for tissue sealing and a second, increased grasping pressure for tissue cutting. Rather, end effector assembly 100 is configured such that, upon approximation of jaw members 110, 120, the appropriate grasping pressure (or a grasping pressure within an appropriate range) for sealing tissue is imparted to tissue disposed between angled portions 117a, 127a and 117b, 127b, while the appropriate grasping pressure (or a grasping pressure within an appropriate range) for cutting tissue is imparted to tissue disposed between cap portion 118 and inverted cap portion 128, respectively. Further, cap portion 118 and inverted cap portion 128, due to their geometries, establish areas of increased current concentrations. Geometries which may create areas of increased current concentrations are typically avoided in designing tissue sealing devices; however, with respect to electrical tissue cutting, it has been found that increased current concentrations facilitate electrical cutting of tissue. The area of increased current concentrations provided adjacent and between cap portion 118 and inverted cap portion 128 is limited to this tissue-cutting region, separate from the tissue-sealing regions defined between angled portions 117a, 127a and 117b, 127b, which define planar parallel surfaces designed to inhibit current concentrations. Additionally, the geometry of the nested wedge configuration of jaw members 110, 120 creates an area of increased tension on tissue between and adjacent cap portion 118 and inverted cap portion 128 (as compared to the tension on tissue grasped between angled portions 117a, 127a and 117b, 127b) which has been found to facilitate and enhance electrical tissue cutting.

As can be appreciated in view of the above, various different configurations of tissue-contacting plates, e.g., tissue-contacting plates 114, 124; 314, 324 (FIG. 5A); 414, 424 (FIG. 5B); 514, 524 (FIG. 5C), etc., may be provided to achieve a desired current concentration effect, pressure, and/or tension. These and other such end effector assemblies will be detailed below. Further, the tissue-contacting plates may incorporate or be coupled to an active or passive heating and/or cooling system (not shown) for selectively heating and/or cooling portions of the tissue-contacting plates, e.g., the angled portions or the apex/trough portions, to enhance tissue sealing and/or tissue cutting or to achieve a particular surgical result.

Referring to FIGS. 1 and 3A-3B, the use and operation of end effector assembly 100 of forceps 10 is described. Initially, with jaw members 110, 120 disposed in the spaced-apart position, forceps 10 is manipulated and/or jaw members 110, 120 are rotated, e.g., via manipulation of rotating assembly 70, such that jaw members 110, 120 are positioned with tissue to be sealed and/or cut disposed therebetween. Once tissue to be sealed and/or cut is disposed between jaw members 110, 120, jaw members 110, 120 may be moved to the approximated position to grasp the tissue, e.g., via depressing movable handle 40 from the initial position to the depressed position relative to fixed handle 50. As mentioned above, the increased mechanical advantage provided by end effector assembly 100 facilitates grasping tissue between jaw members 110, 120.

With tissue grasped between jaw members 110, 120, energy may be supplied to jaw members 110, 120 to treat, e.g., seal, and/or cut tissue. More specifically, in embodiments where a single activation initiates both tissue sealing and tissue cutting, activation switch 82 is activated such that energy is supplied to tissue-contacting plate 114 and/or tissue-contacting plate 124. The energy is conducted through tissue grasped between tissue-contacting plates 114, 124 and, more particularly, through angled portions 117a, 127a and 117b, 127b to create tissue seals therebetween. Additionally, due to the increased grasping pressure, tension on tissue, and area of increased current concentrations adjacent cap portion 118 and inverted cap portion 128, energy conducted between cap portion 118 and inverted cap portion 128 effects cutting of tissue grasped therebetween. As a result, a pair of tissue seals is formed and tissue is cut between the pair of tissue seals. Cutting and sealing may be effected sequentially (in either order), or simultaneously.

Figure 4:
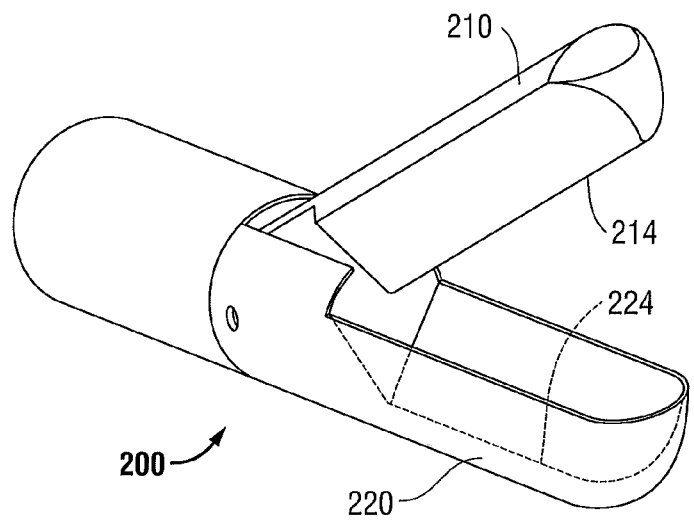
FIG. 4 is a side view of another end effector assembly configured for use with the forceps of FIG. 1 or 2.

In embodiments where activation switch 82 is a two-mode switch, and/or where different sealing and cutting algorithms are provided, activation switch 82 may first be activated in the first mode for tissue sealing (and/or the first algorithm for tissue sealing may be provided), whereby energy is conducted between tissue-sealing plates 114, 124 to seal tissue grasped between angled portions 117a, 127a and 117b, 127b. Thereafter, the second mode may be initiated (and/or the second algorithm for tissue cutting may be provided), manually or automatically, whereby the increased pressure and current concentrations between cap portion 118 and inverted cap portion 128 effect cutting of tissue grasped therebetween. Alternatively, this configuration may be reversed, e.g., wherein cutting is effected first mode and sealing is effected second mode. Further, by initiating only one of the first and second modes, only the corresponding effect, e.g., sealing or cutting, may be achieved, Turning now to FIG. 4, another embodiment of an end effector assembly provided in accordance with the present disclosure is shown generally identified by reference numeral 200. End effector assembly 200 includes first and second jaw members 210, 220 and is similar to end effector assembly 100 (FIGS. 3A-3B) except that, rather than defining a planar distal surface, each jaw member 210, 220 of end effector assembly 200 defines a curved, e.g., a radiused, distal end. Tissue-contacting plate 214 of jaw member 210 extends at least partially about the radiused distal end of jaw member 210, while tissue-contacting plate 224 extends at least partially about an inner surface of the radiused distal end of jaw member 220. Such a feature is configured to facilitate tissue sealing in the area distally beyond the cut area, e.g., distally beyond the apex and trough of jaw members 210, 220, respectively. As such, during procedures where the tissue is sufficiently large to extend distally from jaw members 210, 220, sealing is effected both distally and laterally, e.g., surrounding, the tissue cut line.

With reference to FIGS. 5A-5D, various different configurations of tissue-contacting plates suitable for use with end effector assemblies similar to end effector assembly 100 (FIGS. 3A-3B) are shown and described below. A particular configuration of tissue-contacting plates, e.g., those detailed below or tissue-contacting plates 114, 124 (FIGS. 3A-3B) detailed above, may be provided to facilitate sealing and/or cutting of a particular size or composition of tissue and/or to achieve a desired current concentration effect, tension, and/or pressure, depending on a particular surgical purpose. The corresponding jaw members (not shown) of each pair of tissue-contacting plates are similar to jaw members 110, 120 of end effector assembly 100 (FIGS. 3A-3B) and, thus, are not shown for purposes of simplicity. However, as can be appreciated, such jaw members (not shown) may vary slightly to accommodate the particular configuration of tissue-contacting plates to be used therewith.

Figure 5A:
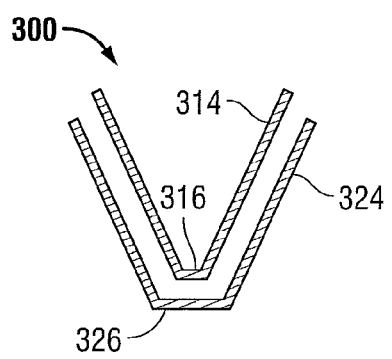
FIG. 5A is a transverse, cross-sectional view of a pair of tissue-contacting plates of another end effector assembly configured for use with the forceps of FIG. 1 or 2.

FIG. 5A illustrates an end effector assembly 300 including a pair of complementary tissue-contacting plates 314, 324 defining a nested wedge configuration. Tissue-contacting plates 314, 324 differ from tissue-contacting plates 114, 124 of end effector assembly 100 (FIGS. 3A-3B) in that, rather than providing a curved cap portion 118 and an curved inverted cap portion 128 (FIGS. 3A-3B), apex 316 of tissue-contacting plate 314 and trough 326 of tissue-contacting plate 324 define planar configurations extending generally parallel to one another. The above-described features of end effector assembly 100 (FIGS. 3A-3B) otherwise apply similarly to end effector assembly 300.

Figure 5B:
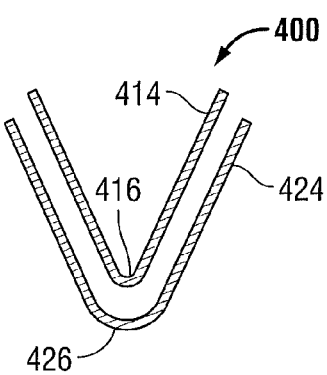
FIG. 5B is a transverse, cross-sectional view of a pair of tissue-contacting plates of yet another end effector assembly configured for use with the forceps of FIG. 1 or 2.

FIG. 5B illustrates another end effector assembly 400 including a pair of complementary tissue-contacting plates 414, 424 defining a nested wedge configuration. Tissue-contacting plates 414, 424 differ from tissue-contacting plates 114, 124 of end effector assembly 100 (FIGS. 3A-3B) in that, rather than defining any suitable curved configuration, apex 416 of tissue-contacting plate 414 and trough 426 of tissue-contacting plate 424 are fully radiused. The radii of curvature of apex 416 and trough 426 may be similar, or the radius of curvature of trough 426 may be larger than that of apex 416. The above-described features of end effector assembly 100 (FIGS. 3A-3B) otherwise apply similarly to end effector assembly 400.

Figure 5C:
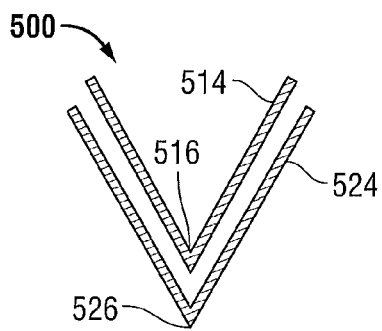
FIG. 5C is a transverse, cross-sectional view of a pair of tissue-contacting plates of still another end effector assembly configured for use with the forceps of FIG. 1 or 2.

FIG. 5C illustrates yet another end effector assembly 500 including a pair of complementary tissue-contacting plates 514, 524 defining a nested wedge configuration. Tissue-contacting plates 514, 524 differ from tissue-contacting plates 114, 124 of end effector assembly 100 (FIGS. 3A-3B) in that, rather than providing a curved cap portion 118 and an curved inverted cap portion 128 (FIGS. 3A-3B), apex 516 of tissue-contacting plate 514 and trough 526 of tissue-contacting plate 524 define angled or pointed configurations. The above-described features of end effector assembly 100 (FIGS. 3A-3B) otherwise apply similarly to end effector assembly 500.

Figure 5D:
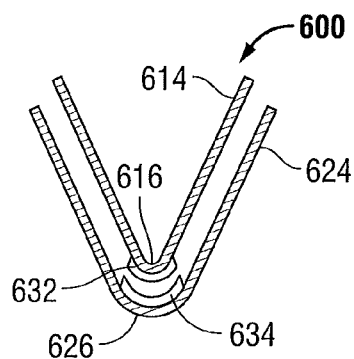
FIG. 5D is a transverse, cross-sectional view of a pair of tissue-contacting plates of still yet another end effector assembly configured for use with the forceps of FIG. 1 or 2.

With reference to FIG. 5D, still another end effector assembly 600 provided in accordance with the present disclosure is shown including a pair of complementary tissue-contacting plates 614, 624 defining a nested wedge configuration. Tissue-contacting plates 614, 624 differ from tissue-contacting plates 114, 124 of end effector assembly 100 (FIGS. 3A-3B) in that tissue-contacting plates 614, 624 further include a insulative member 632, 634 extending across the respective apex 616 and trough 626 thereof. However, it is also contemplated that only one of tissue-contacting plates 614, 624 include an insulative member 632, 634 or that either or both insulative members 632, 634 be incorporated into the respective tissue-contacting plate 614, 624 thereof to define a planar configuration. In addition to the configuration of apex 616 and trough 626 which facilitate electrical tissue cutting, positioning insulative member 632, 634 adjacent the area of tissue cutting may be utilized to further facilitate tissue cutting.

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theatre or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of a surgical forceps, comprising:

first and second jaw members each defining a width and including an electrically-conductive tissue-contacting plate disposed on an opposed surface thereof, the first jaw member defining a wedge configuration extending the width of the first jaw member and having first and second planar surfaces angled inwardly to an apex, the electrically-conductive tissue-contacting plate of the first jaw member defining a first planar portion disposed about the first planar surface, a second planar portion disposed about the second planar surface, and a cap portion disposed about the apex and interconnecting the first and second planar portions, the second jaw member complementary to the first jaw member and defining a nest configuration extending the width of the second jaw member, the second jaw member having a cut-out defined by third and fourth planar surfaces angled inwardly to a trough, the electrically-conductive tissue-contacting plate of the second jaw member defining a third planar portion disposed about the third planar surface, a fourth planar portion disposed about the fourth planar surface, and an inverted cap portion disposed about the trough and interconnecting the third and fourth planar portions, at least one of the first or second jaw members movable relative to another one of the first or second jaw members between a spaced-apart position and an approximated position for grasping tissue therebetween, wherein, when in the approximated position, the first and third planar portions are disposed in parallel orientation relative to one another and impart a first grasping pressure to the tissue disposed therebetween, the second and fourth planar portions are disposed in parallel orientation relative to one another and impart the first grasping pressure to the tissue disposed therebetween, and the cap is received within the inverted cap and imparts a second grasping pressure to the tissue disposed therebetween, the second grasping pressure being greater than the first grasping pressure, the electrically-conductive tissue-contacting plate of at least one of the first or second jaw members adapted to connect to a source of energy for conducting energy between the first and third planar portions and through the tissue grasped therebetween to create a first tissue seal, the second and fourth planar portions and through the tissue grasped therebetween to create a second tissue seal, and between the cap and inverted cap and through the tissue grasped therebetween to cut the tissue between the first and second tissue seals.

2. The end effector assembly according to claim 1, wherein each of the electrically-conductive tissue-contacting plates is monolithically formed as a single component.

3. The end effector assembly according to claim 1, wherein each of the first and second jaw members includes a proximal flange portion and a distal jaw portion, the distal jaw portion including a jaw housing, an insulative body supported on the jaw housing, and the electrically-conductive tissue-contacting plate disposed about and conformed to the insulative body.

4. The end effector assembly according to claim 3, wherein the proximal flange portions of the first and second jaw members are pivotably coupled to one another for pivoting the first and second jaw members relative to one another between the spaced-apart and approximated positions.

5. The end effector assembly according to claim 1, wherein at least one of the cap or the inverted cap is configured to establish at least one of: a region of increased current concentrations adjacent thereto upon conduction of the energy therebetween to facilitate tissue cutting, or a region of increased tension on the tissue to facilitate the tissue cutting.

6. A surgical system, comprising:
an energy source; and
a surgical forceps including an end effector assembly, the end effector assembly including first and second jaw members each defining a width and including an electrically-conductive tissue-contacting plate disposed on an opposed surface thereof,
the first jaw member defining a wedge configuration extending the width of the first jaw member and having first and second planar surfaces angled inwardly to an apex, the electrically-conductive tissue-contacting plate of the first jaw member defining a first planar portion disposed about the first planar surface, a second planar portion disposed about the second planar surface, and a cap portion disposed about the apex and interconnecting the first and second planar portions,
the second jaw member complementary to the first jaw member and defining a nest configuration extending the width of the second jaw member, the second jaw member having a cut-out defined by third and fourth planar surfaces angled inwardly to a trough, the electrically-conductive tissue-contacting plate of the second jaw member defining a third planar portion disposed about the third planar surface, a fourth planar portion disposed about the fourth planar surface, and an inverted cap portion disposed about the trough and interconnecting the third and fourth planar portions,
at least one of the first and second jaw members movable relative to another one of the first or second jaw members between a spaced-apart position and an approximated position for grasping tissue therebetween, wherein, when in the approximated position, the first and third planar portions are disposed in parallel orientation relative to one another and impart a first grasping pressure to the tissue disposed therebetween, the second and fourth planar portions are disposed in parallel orientation relative to one another and impart the first grasping pressure to the tissue disposed therebetween, and the cap is received within the inverted cap and imparts a second grasping pressure to the tissue disposed therebetween, the second grasping pressure being greater than the first grasping pressure, the electrically-conductive tissue-contacting plate of at least one of the first or second jaw members coupled to the energy source for conducting energy between the first and third planar portions and through the tissue grasped therebetween to create a first tissue seal, the second and fourth planar portions and through the tissue grasped therebetween to create a second tissue seal, and between the cap and inverted cap and through the tissue grasped therebetween to cut the tissue between the first and second tissue seals.

7. The system according to claim 6, wherein the energy source is a generator.

8. The system according to claim 7, wherein the energy is electrosurgical energy.

9. The system according to claim 7, wherein the surgical forceps further includes an activation assembly for selectively supplying the energy from the generator to the electrically-conductive tissue-contacting plate of at least one of the first or second jaw members.

10. The system according to claim 9, wherein the generator is configured to supply a first energy algorithm to the electrically-conductive tissue-contacting plate of at least one of the first or second jaw members for sealing the tissue and a second energy algorithm to the electrically-conductive tissue-contacting plate of at least one of the first or second jaw members for cutting the tissue.

11. The system according to claim 10, wherein the activation assembly includes a two-mode activation switch configured to selectively supply the energy from the generator to the electrically-conductive tissue-contacting plate of at least one of the first or second jaw members in a first mode corresponding to the first energy algorithm and a second mode corresponding to the second energy algorithm.

12. The system according to claim 6, wherein each of the first and second jaw members includes a proximal flange portion and a distal jaw portion, the distal jaw portion including a jaw housing, an insulative body supported on the jaw housing, and the electrically-conductive tissue-contacting plate disposed about and conformed to the insulative body.

13. The system according to claim 12, wherein the proximal flange portions of the first and second jaw members are pivotably coupled to one another for pivoting the first and second jaw members relative to one another between the spaced-apart and approximated positions.

14. The system according to claim 13, wherein the surgical forceps further includes a shaft having the end effector assembly disposed at a distal end thereof and a handle assembly disposed at a proximal end thereof, the handle assembly operably coupled to the end effector assembly and selectively actuatable for moving the first and second jaw members between the spaced-apart and approximated positions.

15. The system according to claim 6, wherein the surgical forceps further includes first and second shaft members, the first shaft member coupled to the first jaw member and the second shaft member coupled to the second jaw member, the first and second shaft members movable relative to one another between an open position and a closed position for pivoting the first and second jaw members relative to one another between the spaced-apart and approximated positions.

16. The system according to claim 6, wherein at least one of the cap or the inverted cap is configured to establish at least one of: a region of increased current concentrations adjacent thereto upon conduction of the energy therebetween to facilitate tissue cutting, or a region of increased tension on the tissue to facilitate the tissue cutting.

17. A method of treating tissue, comprising:

grasping tissue between first and second jaw members, the first and second jaw members each defining a width and including an electrically-conductive tissue-contacting plate disposed on an opposed surface thereof, the first jaw member defining a wedge configuration extending the width of the first jaw member and having first and second planar surfaces angled inwardly to an apex, the electrically-conductive tissue-contacting plate of the first jaw member defining a first planar portion disposed about the first planar surface, a second planar portion disposed about the second planar surface, and a cap portion disposed about the apex and interconnecting the first and second planar portions, the second jaw member complementary to the first jaw member and defining a nest configuration extending the width of the second jaw member, the second jaw member having a cut-out defined by third and fourth planar surfaces angled inwardly to a trough, the electrically-conductive tissue-contacting plate of the second jaw member defining a third planar portion disposed about the third planar surface, a fourth planar portion disposed about the fourth planar surface, and an inverted cap portion disposed about the trough and interconnecting the third and fourth planar portions, wherein the tissue is grasped such that a first portion of the tissue is grasped between the first and third portions under a first grasping pressure with the first and third portions in parallel orientation, a second portion of the tissue is grasped between the second and fourth portions under the first grasping pressure with the second and fourth portions in parallel orientation, and a third portion of the tissue disposed between the first and second portions of the tissue is grasped between the cap and inverted cap under a second grasping pressure, the second grasping pressure being greater than the first grasping pressure, wherein portions of the first and second jaw members grasping the third portion of the tissue are configured to establish increased current concentrations adjacent thereto upon conduction of energy therebetween; and conducting the energy between the electrically-conductive tissue-contacting plates of the first and second jaw members such that the first and second portions of the tissue are sealed and such that increased current concentrations adjacent the third portion of the tissue facilitate electrical cutting of the tissue to divide the tissue between tissue seals.

\* \* \* \* \*